United States Patent [19]
Akiyoshi et al.

[11] Patent Number: 5,618,003
[45] Date of Patent: Apr. 8, 1997

[54] PROCESS AND APPARATUS FOR RECLAIMING THE COMPONENTS OF USED DISPOSABLE SANITARY ARTICLES

[75] Inventors: Frank M. Akiyoshi, Bothell, Wash.; Lann E. Richardson; Pat Deen, both of Albany, Oreg.

[73] Assignee: Bot Chan, Inc., Bothell, Wash.

[21] Appl. No.: 401,169

[22] Filed: Mar. 9, 1995

[51] Int. Cl.$^6$ ............................ B02C 19/00; B02C 19/12
[52] U.S. Cl. ......................... 241/19; 241/23; 241/24.19; 241/38; 241/65; 241/DIG. 38
[58] Field of Search ................................ 241/19, 23, 24, 241/38, 65, 79, 79.1, DIG. 38, 606, 24.19

[56] References Cited

U.S. PATENT DOCUMENTS

| 3,441,130 | 4/1969 | Sisson et al. | 209/2 |
|---|---|---|---|
| 3,814,240 | 6/1974 | Laundrie | 209/11 |
| 3,859,174 | 1/1975 | Taylor | 209/2 |
| 3,890,220 | 6/1975 | Anderson | 209/3 |
| 4,034,862 | 7/1977 | Bahri et al. | 209/11 |
| 4,162,019 | 7/1979 | Joa | 414/412 |
| 4,235,707 | 11/1980 | Burke, Jr. | 209/3 |
| 4,250,023 | 2/1981 | Samis et al. | 209/3 |
| 4,283,275 | 8/1981 | Heinbeckel et al. | 209/3 |
| 4,303,501 | 12/1981 | Steffens | 209/2 |
| 4,305,507 | 12/1981 | Wittkopf | 209/3 |
| 4,332,638 | 6/1982 | Maurer et al. | 162/4 |
| 4,332,677 | 6/1982 | Budzich et al. | 209/3 |
| 4,465,591 | 8/1984 | Holz et al. | 209/3 |
| 4,500,040 | 2/1985 | Steffens | 241/14 |
| 4,990,244 | 2/1991 | Anderson | 209/2 |
| 5,084,135 | 1/1992 | Brooks et al. | 162/4 |
| 5,085,785 | 2/1992 | Reeves | 210/767 |
| 5,089,228 | 2/1992 | Meijer | 241/DIG. 38 X |
| 5,268,074 | 12/1993 | Brooks et al. | 162/4 |
| 5,277,758 | 1/1994 | Brooks et al. | 162/4 |
| 5,292,075 | 3/1994 | Bartlett | 241/20 |
| 5,305,886 | 4/1994 | Kehl et al. | 209/2 |
| 5,322,225 | 6/1994 | Cina | 241/14 |
| 5,336,842 | 8/1994 | Massholder et al. | 241/DIG. 38 X |

Primary Examiner—John M. Husar
Attorney, Agent, or Firm—Dowrey & Associates

[57] ABSTRACT

A process and apparatus for disinfection and reclamation of materials contained in contaminated disposable products worn by infants and adults containing human feces and/or urine. The process and apparatus disinfect, mechanically and biologically break down and separates these materials by the use of a pressurized steam digester, mechanical chopper and a screening process. The steam digester process is carried on in a sealed system utilizing a fume scrubber for controlling disposition of ammonia and methane gasses. Effluent and waste are controlled to maintain safe discharges and all recyclable materials are disinfected and reduced to a form suitable for remanufacture of like products or as raw materials for other manufactured products. Polymer particles are exposed to ultraviolet light for molecular breakdown and ion exchange between polymer chains, resulting in further reduction in mass of each particle.

21 Claims, 1 Drawing Sheet

PROCESS AND APPARATUS FOR RECLAIMING THE COMPONENTS OF USED DISPOSABLE SANITARY ARTICLES

BACKGROUND OF THE INVENTION

1. Field of the Invention

The present invention relates to a process and apparatus for mechanically and biologically breaking down the components of used disposable sanitary articles and such single use products which contain human feces and/or urine. These articles include but are not limited to products or portions of products worn by infants and adults as sanitary diapers, pads napkins or sheets and the like. The present process and apparatus is intended for disinfection and reclamation of materials contained in such disposable products. Disease causing bacteria are eliminated while reclaiming the components of such products in a form usable in the remanufacture of like products or as raw materials for other uses or for other manufactured products. In this manner the components of the used disposable sanitary articles are recycled resulting in a significant lessening of resource demand, a significant reduction in environmental pollution and a reduction in solid waste that normally terminates in sanitary land fills.

2. Description of the Prior Art

Disposable sanitary products of the character described, also referred to as "single use" or "one use" human waste collecting or absorbing products, are now in widespread use in this and other countries of the world. These disposable products have in fact become the predominant method for collecting and absorbing human waste from both children and adults when required and have all but replaced cloth diapers. Although in some instances these used, contaminated sanitary items are disposed of by incineration, the more common practice is to deposit them in waste disposal systems which usually terminate in land fills. Since the numbers of such items range in the billions annually in the U.S. alone, the volume of waste material from this source has begun to burden our sanitary land fills. The resulting environmental contamination and pollution from human waste threatens underground water supplies and surface water runoff. Other health problems, due to the bacteria found in human waste, may include disease and infection by direct contact. Incineration, on the other hand, is usually costly and inefficient and itself creates atmospheric pollution.

The primary components of the disposable sanitary products of the type under consideration include cellulose fibers, absorbent granular materials (AGM), plastics and miscellaneous waste materials such as metal fasteners and the like. At present there is no efficient and economically feasible process or apparatus available for mechanically and biologically breaking down these materials. The problem of treating these materials to kill disease causing bacteria such that effluent and wastes are controlled so as to maintain safe discharges in the form of treated water has not been adequately addressed. Likewise disinfection of reclaimed materials and providing for a contamination free processing environment has not been accomplished with known methods and apparatus.

A number of recycling systems have been proposed for reclaiming the valuable wood pulp, cellulose flock absorbent materials and plastics used in the production of single use sanitary products. These efforts have been directed primarily to the reclamation of reusable components of clean waste or production overruns resulting from the original manufacturer of the disposable products. The materials being processed in these systems are unused and uncontaminated and present no pollution problems. The following patents are examples of such processes;

U.S. Pat. No. 4,500,040 Steffens
U.S. Pat. No. 4,305,507 Wittkopf
U.S. Pat. No. 4,303,501 Steffens
U.S. Pat. No. 3,890,220 Anderson A more recent effort is disclosed in U.S. Pat. No. 4,990,244 to Anderson which is directed to processing contaminated single use sanitary products containing urine and/or feces. The Anderson process utilizes a hot water washing machine with sufficient heat to melt and liquidize the adhesives which bond absorbing materials to the moisture sealing plastic material. These components may then be separated by such means as an oscillating separator and/or screening process. The Anderson process and apparatus is merely a washing and materials separation process and does not concern itself with mechanically and/or biologically breaking down the components of the contaminated composites. No attempt is made to disinfect or otherwise biologically treat the wastes and disease causing bacteria. The Anderson process can be characterized as an open vat process with no provision for control of noxious fumes or contact with contaminated human waste. Open processing of this type of material can itself constitute health hazards for personnel in the immediate vicinity.

SUMMARY OF THE INVENTION

The present invention provides a processing system and apparatus for mechanically and biologically breaking down the components of single use or disposable sanitary products containing human wastes. These materials are treated during the process to kill disease causing bacteria and the effluent and wastes are controlled to maintain safe discharges. In addition, all recyclable materials are disinfected and reduced to a form so as to be usable in the remanufacture of like products or as raw materials for other uses or for other manufactured products. The reusable components of the disposable products comprise essentially three main groups, polymers, cellulose fibers, and absorbent granular materials. For the purpose of this specification the term "absorbent granular materials" (AGM) will be understood to mean any known granular absorbent material of unspecified composition presently used in disposable diapers and the like for absorbing moisture and urine. These processed granular materials have a great affinity for water and are capable of taking on up to several hundred times their mass in liquids.

According to the present invention, the contaminated articles are usually supplied to the system by independent vendors in sealed containers. The contaminated materials may be fed by an infeed means such as a belt conveyor which delivers the contaminated product to a steam digester by means of a locked chamber or the like. The lock chamber or hopper prevents escape of any emissions from the digester during the separation and decomposition process. The contaminated product is processed in a low-pressure steam digester where the materials of the components are separated, bacteria (specifically coliform bacteria) are destroyed and ammonia fumes are contained and neutralized. After processing in the steam digester, the separated materials are reduced in size by means of a mechanical chopper or equivalent and are compressed in preparation for a screening process and further mechanical separation.

Effluent in the nature of waste water from the digester, and optionally from the chopper, may be additionally disinfected such as by a chlorinated liquid system to deliver the effluent in the form of treated water to a sanitary sewer system. These processing steps are all carried out without the need for human contact with the contaminated materials or the noxious fumes produced by the steam digester.

The reduced-size and compressed components are then subjected to a screening process for further separation so as to isolate the cellulose fiber, the absorbent granular material, polymers or plastics and some miscellaneous waste material such as metal fasteners and the like. These individual components are then routed for reclamation as follows:

Absorbing materials;

These granular materials are disinfected in the steam digester and after separation may be dewatered and used as suitable recycled absorbing materials. Alternatively the disinfected material may be kept in slurry form and recycled to a new use such as direct soil application, Cellulose fiber;

After final separation, the disinfected fiber material may be dewatered, and placed in a form such as a bale or a container for reuse in the manufacture of paper or like products, Polymers;

Most polymers used in these products are of like molecular structure, therefor, a single process using ultraviolet light will decompose the polymers to a form that is possible to recycle for other products without the generation of new polymers that are non-recyclable. After separation, the reduced size disinfected polymer pieces are processed to an ultraviolet light source which reduces their mass and changes their composition from compound molecular structures to simple molecular components that can be readily converted by most existing systems to new products, Waste;

Foreign materials such as metal fasteners and the like, not normally considered as typical of the product mentioned, will be contained and analyzed before disposal or reclamation.

The overall process or system may be considered as a two-cycle system. The primary cycle or cycle-1 is the mechanical and biological breakdown and disinfection of the materials, the reduction in size by means of the chopper and compression followed by a final separation through a screening process. Cycle-2 or the polymer processing cycle is the treatment of the separated polymers or plastic material. The polymers are subjected to ultraviolet light treatment in order to change their composition from compound molecular structures to simple molecular components that can be readily converted by most existing systems to new products. Cycle-2 of the process, although performed with batch quantities, may however be considered as a part of the overall recycling and reclamation system operating in-line with cycle-1. In this mode, the polymers are collected from cycle-1 until sufficient batch quantities warrant efficient processing. Since the cycle time for cycle-2 is independent of the primary cycle time of cycle-1, which is determined by the digester, cycle-2 may also be operated independently of cycle-1 if desired.

BRIEF DESCRIPTION OF THE DRAWINGS

The drawing is a process flow diagram showing the interrelationship and functions of the components of the system including cycle-1 and cycle-2.

DESCRIPTION OF THE PREFERRED EMBODIMENT

Figure 1:
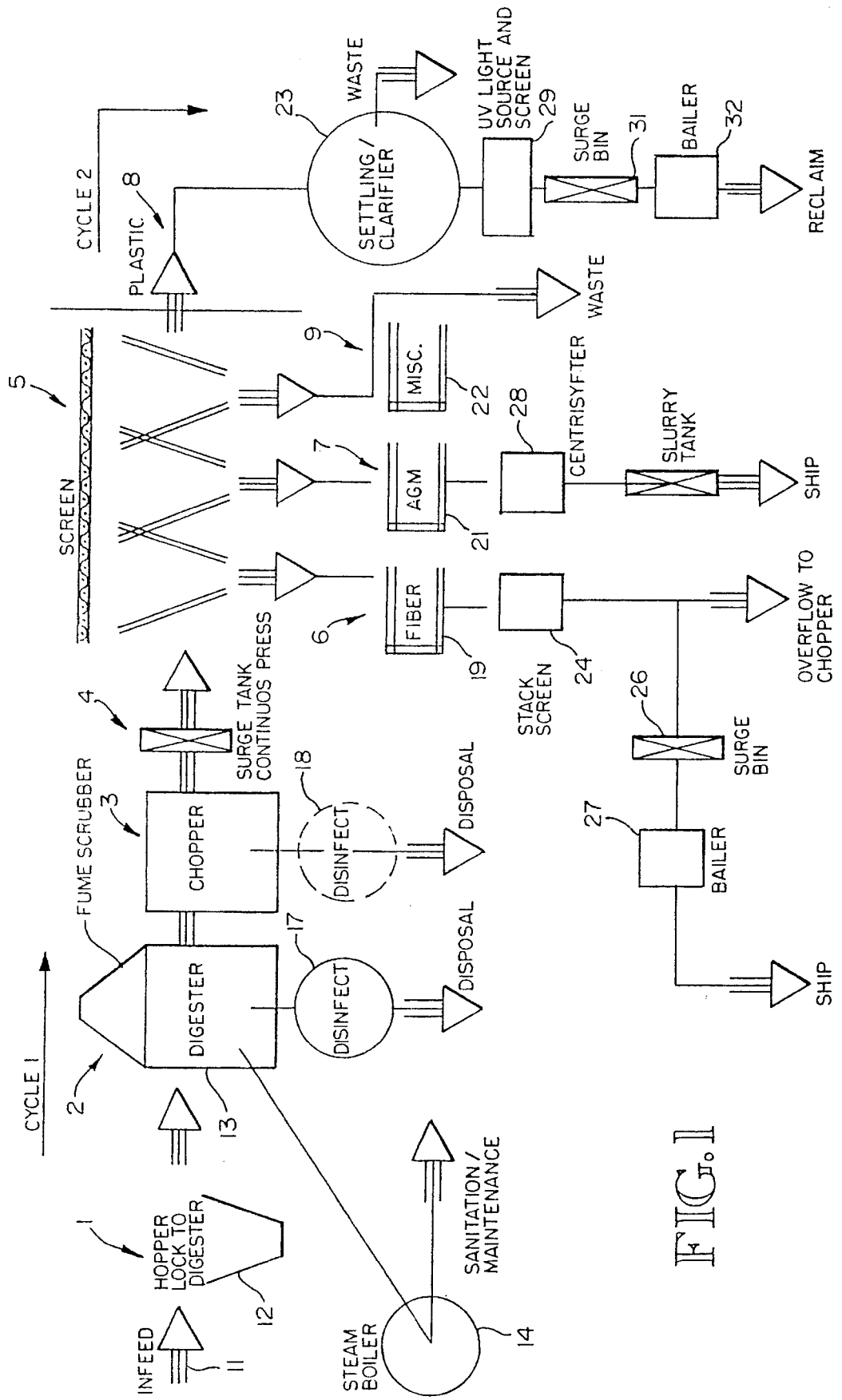

The drawings illustrate schematically the various components of the recycling system in the form of a flow diagram which identifies the components and their interrelationship. It will be understood that, unless otherwise discussed, the components of the system are well known prior art devices or subsystems well understood by those skilled in the art.

Referring to the drawing, the primary components of the system include infeed section 1 with a hopper lock to the digester, a steam digester 2, a chopper 3 for size reduction of the steam treated product and a surge tank and continuous press 4. After the components of the product are broken down in the steam digester and reduced in size, a screening separator 5 separates the product into the components which include cellulose fibers 6, absorbent granular material 7, plastic materials 8 and miscellaneous wastes 9. These four primary separated products are then further treated as will be presently described for reclamation and recycling.

The components of the primary processing system, cycle-1 as illustrated in the drawings, are controlled by batch processing times of the digester 2 as will be more fully described. The steam digester 2 is fed by a steam boiler and functions to decompose and initially separate the main components of the contaminated waste products. The single use sanitary products, such as disposable diapers and the like containing human waste, are normally kept clear of other household wastes and collected for periodic pickup. These waste materials will be supplied by independent vendors in sealed containers such as plastic bags to be fed to the steam digester. For this purpose, infeed section 1 of the system comprises belt conveyor 11 for delivering contaminated waste to a hopper lock device 12 which cooperates with the digester 13 to contain environmental contaminants during the loading process. The belt conveyor 11 conveys the contaminated product in flights or batch size groups compatible with the batch cycle time of the digester 13. Each through cycle may be tagged with an indicator strip for periodic examination of bacteria control at the digester 13. Thus the feed rates are determined by the batch cycle time of the digester which also controls the cycle time of the remaining components of cycle-1 of the system.

Since the steam digester 13 is a pressurized sealed system, the hopper lock 12 is necessary as a sealing device during feeding of product to the digester. The hopper lock consists of a chute-like hopper and an automatic cycling shutter which serves to contain the environmental contaminants such as gasses, liquids and solid wastes from the digester. The cycle response of the hopper lock is again dependent on the digester cycle time and response. Suitable controls will be provided for controlling the speed of the infeed conveyor 1 and cycle response of the hopper lock as a function of the cycle time of the digester. It will also be understood that an identical hopper lock arrangement may be used for unloading the digester after each batch cycle.

As aforementioned, the digester 13 serves to decompose or "break-down" and separate the contaminated product into its components in a batch cycling process. The digester is a steam fed unit which is sealed and operates at a low pressure of approximately 15 psi normally maintained at 140° F. with a cycle time of approximately 15 minutes. The cycle time may be varied depending upon the pressure and temperature at which the digester is operated. The digester is fed by a steam boiler unit 14 in a conventional manner to maintain the proper temperature in the digester. When subject to the steam digester processing, the main components of the contaminated products are decomposed and caused to initially separate due to the melting of the adhesives which bind the absorbent materials to the plastic liners. Steam digesters of the type described are well known in the prior art and are of various configurations, one common application being in the initial wood fiber digesting process of the pulp industry. Within the sealed unit a conveyor such as a chain and sprocket with conveyor flights typically moves the material in a gently inclined path. Some means of agitation or tumbling may also be provided or a gentle rolling effect of the product may be attained by application of steam jets located beneath the moving product. With this treatment, disposable diapers, for instance, initially separate leaving cellulose fiber, polyethylene polymers, absorbent granular material and some waste material such as metal fasteners or the like. With the introduction of moisture from the steam, the treated product exits the digester as a slurry-like mass leaving behind a certain amount of waste water which is disposed of in a manner presently to be described. In addition, subjecting the contaminated mass to the temperatures and pressure described for the cycle time serves to destroy disease causing bacteria, specifically coliform bacteria. At this point the slurry-like mass has been disinfected and is ready for particle size reduction by the chopper 3. It is possible, of course, to shorten the digester cycle processing time by using higher temperatures with a maximum of 180° F. with the same pressure, i.e. 15 psi. The exact pressures, temperatures and cycling time may be chosen and altered by those familiar with treatment of contaminated products in order to destroy or neutralize sufficient bacteria in the discharge from the digester.

In addition to the decomposed and separated solid materials discharged from the digester, gasses are produced in the digester which include water vapor, methane and ammonia. These gasses produced in the digester are controlled by means of an overhead fume scrubber 16 which will be equipped with a PH meter for monitoring methane gas. As an alternative, depending on the size of the processing operation, if adequate quantities of methane gas are produced it may be economically feasible to use these gasses to assist in the fuel supply for the steam boiler. Fume scrubbers of the type described, also known in the art as wet scrubbers, which may be controlled with PH meters are commonly known to the art and require no further explanation.

Biologically treated waste water from the digester 13 containing treated human waste is conveyed via piping to a disinfection system 17 which may be a conventional chlorinated liquid system. The system is monitored to maintain for instance a minimum of one part per million of bacteria so as to be suitable for discharge in local waste systems. Disinfection systems of this type usually employ a chlorination device commonly known as a "drip chlorinator" with metering and monitor controls so as to destroy "waterborne" disease causing bacteria. Control of discharges can be monitored to meet EPA (Environmental Protection Agency), DEQ (Department of Environment Quality) and local and state regulations of such discharges. Normally a controlled discharge of less than one part per million of bacteria with tertiary control of phosphorous and nitrogen to eliminate over production of algae in discharge streams or reservoirs is required. Dechlorination and phosphorous-nitrogen controls can be added based on local and federal regulations of the particular site.

The composite mass of slurry and solid materials containing cellulose fiber, absorbent granular materials and polymers is passed through the chopper 3 for size reduction and partial dewatering. The chopper may be any form of multiple knife or flail device used in prior art processes which functions primarily to chop the plastic into screenable particle sizes. In operation, the slurry mass passes through the chopper and only solid particles of a certain size are allowed to exit. The desired maximum size of particle is two inches square, however the exact size may be varied as desired to accommodate further screen processing requirements. The chopper may be a continuous process that will accept the discharges from the digester as digester cycle times dictate. Effluent from the chopper in the form of biologically treated water may be further disinfected by an optional disinfection system 18 in an identical manner as described for the disinfection system 17 of the digester.

From the chopper 3, the reduced size mass is passed through a surge tank or holding tank and press unit 4 for dewatering and consolidation before going to a screening process for final separation. The unit 4 may be a continuous or semi-continuous process based on the cycle time of the digester 13. This unit comprises a control device which introduces the chopped materials from the digester and the chopper to the screening process for further separation. Regulation of the screening process times are controlled by discharges from this point in the process preferably by electronically monitored systems consisting of both digital and analog sensor devices and programmable logic controls.

The screening process indicated at 5 in the drawing comprises a screening system which may be made up of a series of screening separators such as mesh belts, or both oscillating and stationary screens. The screening system will serve to segregate the "chopped" materials as they are delivered from the steam digester and chopper. In some cases the screening may consist of decreasing mesh size screens to separate the materials in a well known manner. Many types of screening devices and separators have been used in the past including air stream and electro-static devices. Additionally separation of the components may be accomplished by such means as flotation and settling in a well known manner. Most commonly used is a system of oscillating screen separators in series with a decreasing mesh size. In the present process, it is contemplated that sufficient water will be added to keep the various components in a slurry form. The discharge from the screening system thus consists of slurries of cellulose fiber, absorbent granular materials, polymers and a minute quantity of solid wastes introduced as foreign materials to the normal composition of the aforementioned products. These separate materials are individually collected for further recycling and reclamation. The fiber component 6 is channeled to a collector 19, the absorbent granular material 7 is channeled to the collector 21, the miscellaneous solid wastes 9 are channelled to a collector 22 and the chopped plastic is channeled to a cycle-2 settling-clarifier unit 23.

The cellulose fiber component 6 may be further subjected to a stack screen 24 comprising continuously decreasing mesh size screens which confine the cellulose (wood) fiber. Any minor discharge of water in this screening process may be piped back to a disinfection process such as the disinfection systems 17 and 18. Any overflow of fibers or foreign materials is recirculated to the chopper 3 for reprocessing. The cellulose fiber may be collected in a surge bin 26 and finally processed in a binding, packaging or other material handling system such as the bailer 27. From there the fibrous material may be disseminated to remanufacturing processes or stored in appropriate warehouse facilities as market demands dictate.

The absorbent granular material 7 is processed in a centrisifter 28 which is a commercially available device usually comprising a cylindrical, rotating screening and dewatering device which removes any fiber and reduces the mass of the absorbent granular material to a form that can be packaged for reuse in similar manufacturing processes. In the present system this material may also be maintained in a slurry form for direct disposal such as a sanitary soil enhancer for instance. The cycle time for the centrisifter is based on screen discharge at 22 which is based on the parameters set for cycle time at the digester 13.

Any miscellaneous waste material or foreign materials not normally considered as typical of the product will be collected at 22 and contained for analysis for disposal or possible reclamation.

Polymers, in the form of polyethylene (typically) are discharged from the screening process 5 as partially dewatered, disinfected and chopped particles. The particle size will vary according to each batch content and the knife setting or spacing at the chopper 3. Typically the polymer particle size will be approximately 2 inch strips or squares in 1 mil to 2 mil thicknesses. These particles are then processed to the settling clarifier 23 where the water suspended polymer material is treated with a commercial coagulant such as alum or a similar environmentally safe chemical. Since the particles are suspended in water, they may be "skimmed" by a rotary surface skimmer in a well known manner and discharged at an exit point in settling tank. As indicated in the drawing, any waste or foreign materials are removed from the polymers.

The polyethylene polymers which are the typical polymers found in the sanitary products being processed have a simple molecular structural chain that is both parallel and linked to other chains much like the linear structure of wood fibers in timber. After discharging from the settling/clarifier 23, these polymer particles are exposed on a rotary screen device 29 to ultraviolet light in the form of lamps (not shown) both internal and radially directed relative to the rotating screen. The result is a breakdown of molecules and ion exchange between the polymer chains, resulting in a further reduction in the mass of each particle. This final reclaimed particle size is dependent on exposure time and intensity of the ultraviolet light source to which they are exposed. The polymer reclaiming system of cycle-2 is independent from the primary process cycle-1 time which, as aforementioned is determined by the digester 13. The polymers may therefore be stored until sufficient batch quantities warrant sufficient processing. From the rotary screen device 29, the treated polymers are transferred by way of a surge bin 31 to a component such as a bailer 32. The final product is in the form of thin linear strips that can be utilized in similar product manufacturing or recomposed in sheets for other polyethylene products. The bailer 32 comprises a controlled packaging unit where the aforementioned polymers are bound and sealed for appropriate distribution to remanufacture in processes.

The present invention has been described with reference to a preferred embodiment and certain modifications. Further modifications and alterations may become apparent to one skilled in the art upon reading and understanding this specification which is intended to include all such modifications and alterations within the scope of the appended claims.

What is claimed is:

1. A system for reclaiming the components of composite disposable articles contaminated with bacteria-containing human waste, said components including cellulose fiber, absorbent materials and adhesively bonded sheet material carriers therefor, comprising in combination;

a steam digester including a pressure sealed vessel for receiving and holding said human waste contaminated articles, and steam injection apparatus for injecting steam under pressure into said vessel into direct contact with said articles for a predetermined time period to dissolve said adhesive and initially cause separation of said article into said components to form a composite mass, chopper apparatus operatively associated with said digester for mechanically breaking said mass into discrete particles of a given maximum size, apparatus for transferring said mass from said digester to said chopper after said predetermined time period, and separator apparatus operatively associated with said chopper for receiving and separating said discrete particles into said components and collecting particles of each said components separately for recycling.

2. The system of claim 1 including;

control apparatus for maintaining said steam digester under sufficient pressure and temperature for said predetermined time period for killing substantially all said bacteria, dewatering apparatus associated with said digester and said chopper for removing substantial amounts of water from the treated mass as disposable waste water, and a chemical disinfection system for treating said waste water from the mass for reception by a municipal waste disposal system.

3. The system of claim 2 wherein the sheet material carriers are composed primarily of polyethylene polymer material, and ultraviolet light treatment apparatus for exposing said separated polymers to ultraviolet light to reduce the mass thereof to facilitate further recycling.

4. The system of claim 2 further including;

a fume scrubber apparatus connected to said pressure sealed vessel for neutralizing ammonia gas and monitoring methane gas emission levels therefrom.

5. The system of claim 2 wherein said digester further includes;

a conveyor for moving said mass through said sealed vessel, and means for agitating said moving mass within the vessel.

6. The system of claim 5, wherein said steam digester comprises a batch process, and further including;

hopper locking mechanism for loading and unloading said sealed vessel while preventing escape of gasses and liquids therefrom.

7. The system of claim 2 wherein said separator apparatus includes means for maintaining said absorbent material in a slurry state during separation.

8. A process for reclaiming the components of single use disposable sanitary articles contaminated with bacteria-containing human waste, said components including cellulose fiber, absorbent materials and adhesively bonded sheet material carriers therefor, comprising the steps of:

infecting steam under pressure into direct contact with said articles in a pressure sealed vessel to initially dissolve said adhesive to cause separation and decomposition of the articles into said components to form a mass, then mechanically breaking said mass into discrete particles of a maximum size, and then separating said particles into said components and collecting particles of each said component for recycling.

9. The process, according to claim 8 further including the steps of:

maintaining said steam under sufficient pressure and maintaining the temperature in said vessel at sufficient levels for a predetermined cycle time sufficient for killing substantially all said bacteria, removing waste water from the treated mass as disposable waste water, and chemically disinfecting said waste water suitable for reception by a municipal waste system.

10. The process according to claim 9 further including the steps of;

holding said contaminated mass under said steam pressure in a closed steam digester vessel, and neutralizing ammonia gas given off during said steam treatment, and monitoring methane gas emissions from said steam digester.

11. The process according to claim 9 further including the steps of;

maintaining said absorbent materials in a slurry form during separation.

12. The process according to claim 9 wherein said sheet material comprises polyethylene polymer and further including the step of;

treating said separated polymers with ultraviolet light to reduce the mass thereof for recycling.

13. A process for reclaiming the components of single use disposable sanitary articles contaminated with bacteria-containing human waste, comprising the steps of;

injecting steam under pressure into direct contact with said articles in a pressure sealed steam digester vessel to initially cause separation of the articles into said components to form a mass, neutralizing ammonia gas given off during said steam treatment, and monitoring methane gas emissions from said digester.

14. The process according to claim 13 further including the step of;

agitating said mass during steam treatment to enhance separation of the components.

15. The process according to claim 14 further including the step of;

maintaining said steam under sufficient pressure and temperature for a predetermined cycle time for killing substantially all said bacteria.

16. The process according to claim 15 wherein said steam is maintained at a pressure of approximately 15 psi and the temperature in said vessel is maintained at approximately 140° F. for a cycle time of approximately 15 minutes.

17. A system for reclaiming the components of used composite disposable articles contaminated with bacteria-containing human waste, said components including cellulose fiber, absorbent materials and adhesively bonded sheet material carries therefor comprising in combination;

a steam digester including a pressure sealed vessel for said articles and means for applying steam under pressure to dissolve said adhesive, initially cause separation of said articles into said components to form a mass and to simultaneously disinfect said mass, and chopper apparatus operatively associated with said digester for receiving said mass and for subsequently mechanically breaking said mass into discrete particles of a maximum size.

18. The system of claim 17 including;

a fume scrubber connected to said digester for neutralizing ammonia gas issuing therefrom.

19. A process for reclaiming the components of used disposable sanitary articles contaminated with bacteria-containing human waste, comprising the steps of;

injecting steam under pressure into direct contact with said articles in a pressure sealed steam digester vessel to initially cause separation of said articles into said components to form a mass and to simultaneously disinfect said mass, and neutralizing ammonia gas given off during said steam treatment.

20. A system for preparing the components of composite disposable articles contaminated with bacteria-containing human waste for recycling, said components including cellulose fiber, absorbent materials and adhesively bonded sheet material carriers therefor, comprising in combination;

a steam digester, said steam digester including a pressure sealed vessel for receiving and holding said human waste contaminated articles, and steam injection apparatus for injecting steam under pressure into said vessel into direct contact with said articles for a predetermined time period to dissolve said adhesive and initially cause separation of said article into said components to form a composite mass, chopper apparatus operatively associated with said digester for mechanically breaking said mass into discrete particles of a given maximum size, and apparatus for transferring said mass from said digester to said chopper after said predetermined time period.

21. The system of claim 20 including;

control apparatus for maintaining said steam digester under sufficient pressure and temperatures for said predetermined time period for killing said bacteria.

* * * * *

UNITED STATES PATENT AND TRADEMARK OFFICE
CERTIFICATE OF CORRECTION

PATENT NO. : 5,618,003

DATED : April 8, 1997

INVENTOR(S) : Akiyoshi et al.

It is certified that error appears in the above-identified patent and that said Letters Patent is hereby corrected as shown below:

Column 8, Claim 8, line 6, "infecting" should read --injecting--.

Signed and Sealed this

Twenty-sixth Day of August, 1997

Attest:

BRUCE LEHMAN

Attesting Officer

Commissioner of Patents and Trademarks